United States Patent [19]

Nishikawa et al.

[11] Patent Number: 5,173,423
[45] Date of Patent: Dec. 22, 1992

[54] PROCESS FOR BREEDING A GLABROUS VARIETY OF RICE CROP AND A GLABROUS PLANT

[75] Inventors: Akira Nishikawa, Sanda; Toshiya Yamamoto, Toyonaka; Seiichi Tuji; Hirochika Sakano, both of Takarazuka; Hideo Hirohara, Sakai, all of Japan

[73] Assignee: Sumitomo Chemical Company Limited, Osaka, Japan

[21] Appl. No.: 479,670

[22] Filed: Feb. 12, 1990

[51] Int. Cl.$^5$ .......................... C12N 5/04; A01H 4/00; A01H 1/02
[52] U.S. Cl. ................................. 435/240.5; 800/200; 800/DIG. 57; 435/240.4; 435/240.48; 435/240.49; 435/240.45; 47/58
[58] Field of Search ............... 800/200, DIG. 57, 235; 435/240.4, 240.48, 240.49, 240.5, 240.45; 47/58

[56] References Cited

U.S. PATENT DOCUMENTS 4,672,035  6/1987  Davidonis et al. ............... 435/240.4

FOREIGN PATENT DOCUMENTS 54-040136  3/1979  Japan .
60-160818  8/1985  Japan .
61-074519  4/1986  Japan .
62-065680  3/1987  Japan .
1-067130   3/1989  Japan .

OTHER PUBLICATIONS

Li Su Nam et al. (1986) Cereal Research Communications 14(2): 197.
Schaeffer et al. (1986) Plant Cell, Tissue and Organ Culture 6: 149–157.
Zapata et al. in FFTC Book series No. 38 (Bay-Petersen, ed.) pp. 80–81 and 83–85, 1988.
Morrison et al. (Jun. 1988) Bio/Technology 6: 684–690.
Heu et al. (1981) Seoul Natl Univ Coll Agric Bull 6(1): 89–98, Biological Abstract 81999, Jun. 1982.
Jiang et al. (1988) Jpn J. Crop Sci 57(1): 132–138, Biological Abstract No. 117609, Jun. 1988.

Primary Examiner—David T. Fox
Assistant Examiner—Che Suyden Chereskin
Attorney, Agent, or Firm—Venable, Baetjer, Howard & Civiletti

[57] ABSTRACT

Disclosed herein is a process for breeding a glabrous variety of rice crop, this process comprising the steps of culturing tissues from a target rice plant, culturing the calli formed to a regeneration medium, growing the regenerates and selecting glabrous plants therefrom them, a new and distinct variety of a glabrous variety of a rice plant obtained by this process, and a process for the production of a glabrous plant which comprises further reproducing the plants. This glabrous variety is useful for rice cultivation.

4 Claims, 4 Drawing Sheets

PROCESS FOR BREEDING A GLABROUS VARIETY OF RICE CROP AND A GLABROUS PLANT

BACKGROUND OF THE INVENTION

1. Field of the Invention

The present invention relates to a process for breeding a glabrous variety of rice crop useful for rice cultivation, particularly by a mechanical harvesting and processing by applying a tissue culture technique.

2. Description of the Related Art

Tissue culture has become extensively as a rice breeding tool, and known tissue culture techniques include anther culture, immature embryo culture, seed embryo culture, young-leaf culture, and root-tip culture.

Among these, anther culture is used mainly for the production of doubled haploid lines or the induction of somaclonal variations beneficial for breeding purposes, but the efficiency of the anther culture requires an improvement if it is to be a practically used for breeding, and the information on induced somaclonal variations has not been sufficiently documented.

As mentioned above, a glabrous variety of rice crop is highly effective for the improvement of rice cultivation, in particular the efficiency of mechanical harvesting, processing, and other work. Similar varieties have been developed by crossbreeding in the United States, but these require extremely troublesome procedures and much time.

In Japan, the Hokuriku Agricultural Experiment Station of the Ministry of Agriculture, Forestry, and Fisheries has reported that an anther culture might be used to obtain glabrous germplasm lines for further use in crossbreeding (Crop Science Laboratory No. 6, Hokuriku Agricultural Experiment Station 1979, reports on Rice Breeding, 1-19). From a viewpoint of the overall breeding process, however, this also requires troublesome procedures and much time. Namely, the use of a tissue culture technique, has not enabled the obtaining of a practical glabrous variety in the U.S., Japan, and other countries.

The object of the present invention, in consideration of the above-mentioned prior art, is the practical and efficient creation of new glabrous varieties from commercial rice varieties, in a short period and without change in the properties of the original varieties.

SUMMARY OF THE INVENTION

The present inventors, in consideration of the above situation, have engaged in various studies of tissue culture and breeding, and as a result, have discovered that an economically useful variation of glabrousness can be induced at a high frequency without a change in other characteristics of the original variety. Based on this discovery, therefore, they developed a new glabrous rice variety during a short period without crossbreeding, and thus perfected the present invention.

That is, the present invention relates to a process for breeding a glabrous variety of rice crop which comprises culturing tissue from a target rice plant, culturing the formed calli in a regeneration medium, growing the regenerants and selecting glabrous plants therefrom, and establishing a glabrous new rice variety (referred to as the breeding process of the present invention); and also relates to the plants of a new variety developed by the breeding process of the present invention (referred to the plants of the present invention). The anther culture is the most preferable technique for the present invention.

At the first generation, the plant of the present invention can be multiplied by self-pollination, to obtain second generation seeds, and these seeds are sown by a usual method to grow second generation plants. Further, the same procedure is repeated for later generations, to multiply and produce the plant of the present invention.

Furthermore, the present invention may be used as an efficient method of hybrid seed production in a rice crop, and in this case, a glabrous form is used as one or the other of the parent lines, to selectively remove unneccessary parental seeds and obtain hybrid seeds. By this method, it is not only possible to remarkably reduce the labor involved in hybrid seed production, but also to increase the amount of hybrid seed production.

DESCRIPTION OF THE PREFERRED EMBODIMENT

Figure 1:
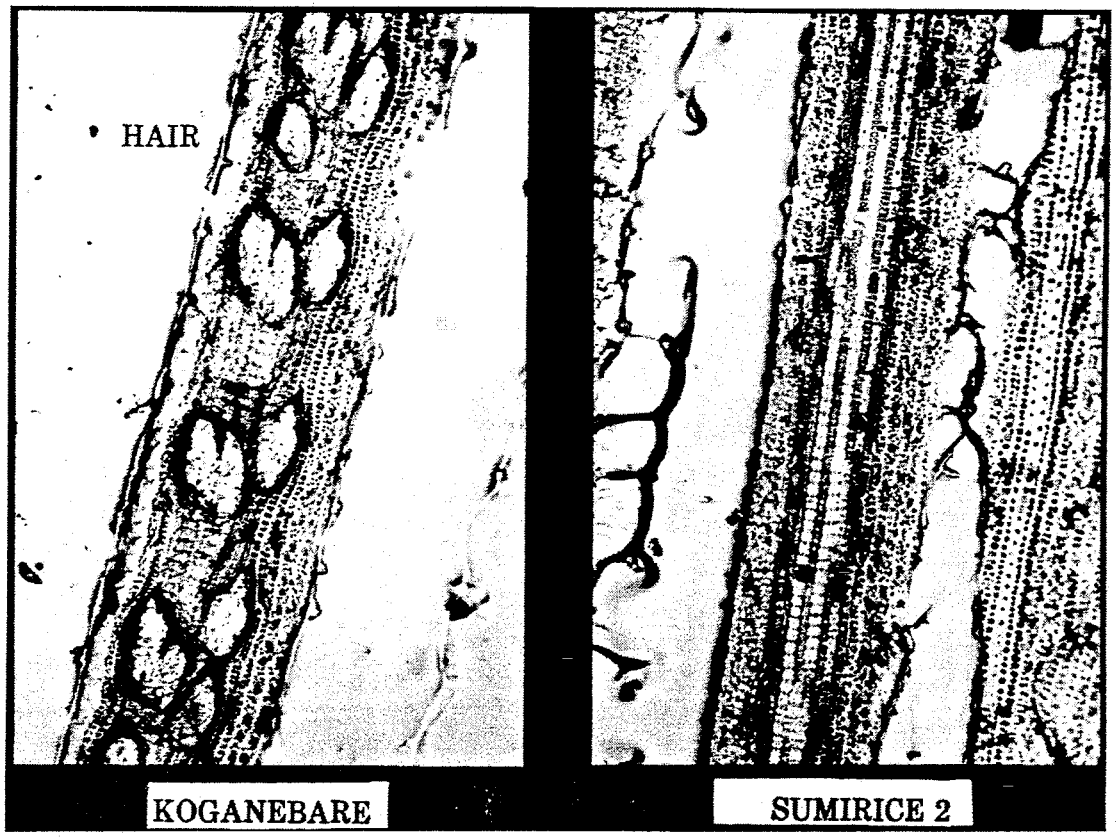
FIG. 1 is a micrograph of the leaf blades of the new and distinct glabrous variety of rice plant "Koganebare"
Figure 2:
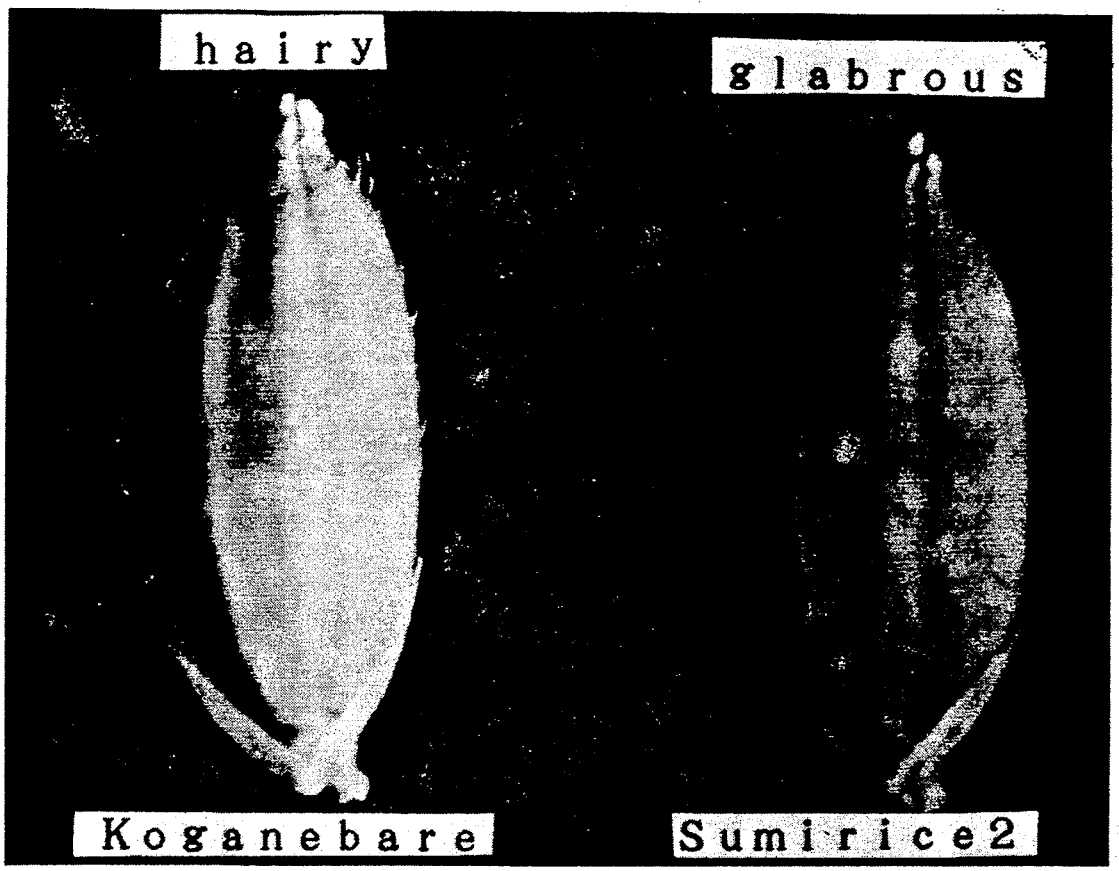
FIG. 2 is a photograph of the unhulled rice of the new glabrous variety.
Figure 3:
FIG. 3 is a photograph of the whole rice plants of the new glabrous variety; and, FIG. 4 is a photograph of the spikes of the new glabrous variety.
Figure 4:
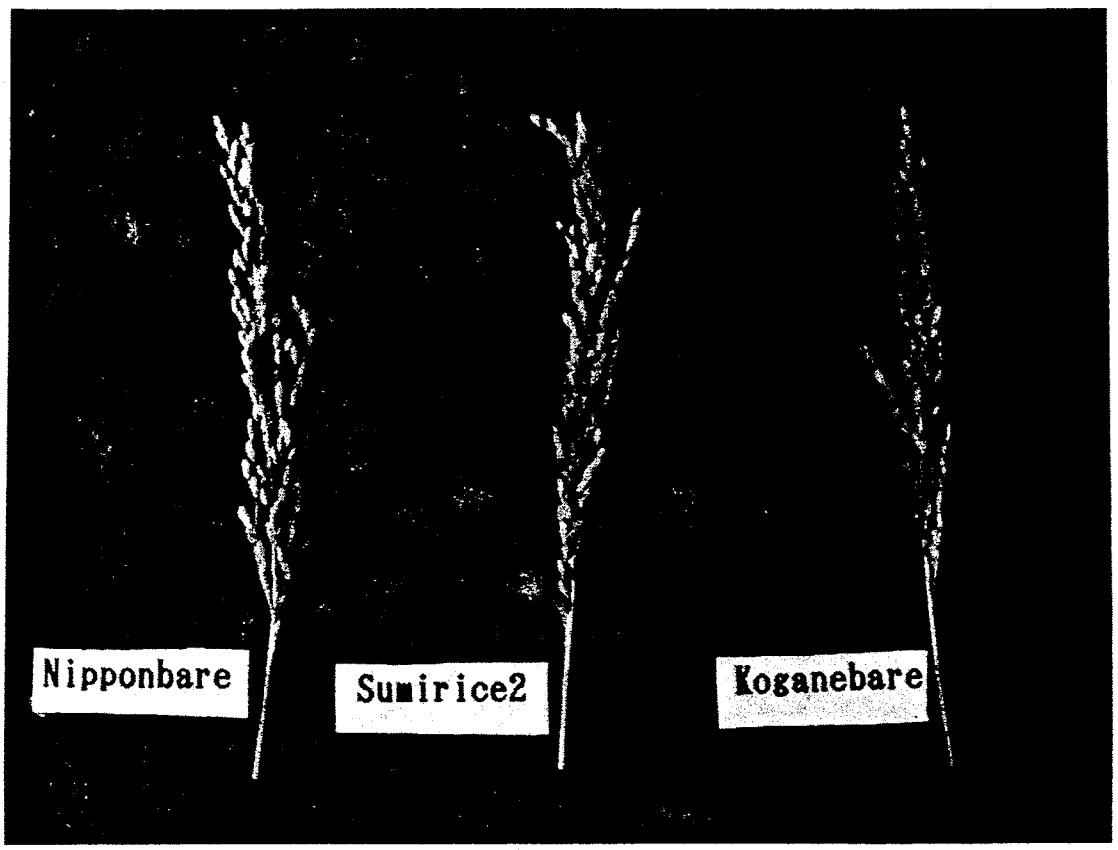

The variety of the target rice plants that can be utilized in the processes of the present invention, include the japonica-type rice varieties such as Aokaze, Akitakomachi, Akitsuho, Akinishiki, Akihikari, Akebono, Asominori, Ooseto, Kitaake, Kitahikari, Kiyonishiki, Koganebare, Koganehikari, Koganemasari, Koshihikari, Gohyakumangoku, Sasanishiki, Sachiminori, Satohonami, Shizuhikari, Shinrei, Tomoyutaka, Nakateshinsenbon, Nadanishiki, Niigatawase, Nishihomare, Nipponbare, Nihonmasari, Hatsuboshi, Fukunohana, Fukuhikari, Fukuhonami, Hourei, Hoshinohikari, Michikogane, Minaminishiki, Oochikara, Koihime, Higonohana, Hinohikari, Kinuhikari, Hakutomochi, Yokaminori, KoKonoemochi, Chikuhonishiki, Notohikari, Tsukinohikari, Jyuugoyamochi, Hyogokitanishiki, Hanafubuki, Hananomai, Aichinokaori, Asanohikari, Yaekogane, Chikubuwase, Toyokogane, Toyosachi, Hoshiyutaka, Chiyohonami, Hayayutaka, Tsukushibare, Minamihikari, Asukaminori, Sachiizumi, Akichikara, Saotome, Ibukiwase, Chiyonishiki, Tamahonami, Hatsukogane, Natsuhikari, Yamachikara, Komaasahi, Kochiminori, Saiwaimochi, Nishihikari, Habataki, Musashikogane, Yamadanishiki, Yamahikari, Kaguramochi, Kurenaimochi, Koganemochi, Takasagomochi, Tsukimimochi, Hidekomochi, Hiyokumochi, Mangetsumochi, and Miyakoganemochi; the varieties found in Korea, such as Milyang 15, Milyang 46, Milyang 54, Milyang 55, Milyang 60, Milyang 73, Suweon 287, Suweon 325, Suweon 332, Suweon 294, Suweon 290, Suweon 198, Suweon 223, Suweon 303, Suweon 320, Suweon 306, Suweon 235, suweon 330, Suweon 305, Iri 342, Iri 348, Iri 291, Iri 347, Iri 346, Iri 350, Iri 362. Iri 344, Iri 353, Iri 365, Iri 367, and Iri 355; the varieties found in Taiwan, such as Tainung 67, Tainung 70, Tainung 68, Hsinchu 64, Hsinchu Glutinous 4, Tainan 9, Tainan 5, Taichung 189, Taichung Glutinous 70, Taichung Sen 10, Taichung Sen 3, Taichung Sen Glutinous 1, Taichung Native 1, Kaohsiung 141, Kaohsiung 139, Kaohsiung Sen 7, and Taitung 29; the varieties found in Southeast Asia, such as Khao Dawk Mali 105, RD 4, RD 6, RD 15, RD 17, RD 19, RD 23, Mahsuri, IR42, MR84, Anak Dara, Kadaria, Setanjung, Mat Candu, IR36, IR50, IR58, IR60, IR62, and IR64; the varieties found on the European continent, such as Balilla, Ringo, Arborio, Lido, Ribe, Rona, S.Andrea. Veneria, Europe, Cript, Padano, Rosa Marchetti, Vialone Nano, Baldo, Bahia, Girona, and Balilla/Sollana; and the varieties found in the Americas, such as LA110 and Calmochi-101. Particularly preferred varieties are Koganebare and Nipponbare.

The tissue from a target rice plant include an anther, immature embryo, seed embryo, young leaf, root tip, pollen, coleoptile, immature spikelet, young glume, and unpollinated ovary. An especially preffered tissue is an anther.

In the present invention, as culture media used for tissue culture, mention may be made of, for example, media MS, B5, white, and Heller. In particular, as the culture media for an anther culture, mention may be made of a ½ concentration of, for example, media MS, H, H5, MM, XM2, K, N6, SK. The plant hormones generally used are, for example, 2,4-D (2,4-dichlorophenoxy acetic acid), NAA (naphthalene acetic acid), Kinetin, BA (benzyl adenine), IAA (indole acetic acid), IBA (indole butyric acid), and GA (gibberellin).

Sterilizing chemicals used for usual plant cell and tissue cultures are calcium perchlorate, sodium perchlorate, sodium hypochlorite, hydrogen peroxide, mercuric chloride, and antibiotics.

The present invention is further illustrated by the following practical examples thereof. Note, these examples do not limit the scope of the present invention in any way.

In the present invention, the morphological and physiological (disease resistance) characteristics of the new variety "glabrous koganebare" of rice crop given as embodiments are described in the following examples.

EXAMPLE 1

A jaonica-type rice variety "Nipponbare" was used as a plant material for an anther culture of the present invention. The seeds were sown in May 1986, and the seedlings were transplanted in Jun. to an experimental field located at 636-2, Aza Shionoyama, Kishiro, Kasai, Hyogo 675-23, Japan. Immature spikeletes containing the microspores at the middle to late uninucleate stage were sampled on Aug. 21, 1986, and these immature spiketets with leaf sheaths were covered with gauze moistened with water, further covered with aluminum foil, placed in a plastic bag, and treated at a temperature of 5° C. for 7 days.

The pretreated immature spikelets were immersed in an 80% aqueous solution of ethanol for approximately 1 min., and washed 2 to 3 times with sterilized water on a clean bench. Immature anthers were excised with a pair of tweezers and incubated on a callus-inducing SK medium (Sk basal medium) (see Table 1),

TABLE 1

| Item | Composition of Basal Media Tested | |
| --- | --- | --- |
| | N6 | SK |
| KNO$_3$ | 2830 mg/l | 2830 mg/l |
| (NH$_4$)$_2$SO$_4$ | 463 | 315 |

TABLE 1-continued

| Item | Composition of Basal Media Tested | |
| --- | --- | --- |
| | N6 | SK |
| KH$_2$PO$_4$ | 400 | 640 |
| CaCl$_2$.2H$_2$O | 166 | 166 |
| MgSO$_4$.7H$_2$O | 185 | 280 |
| Fe-EDTA | 42.1 | 72.8 |
| MnSO$_4$.4H$_2$O | 4.4 | 4.4 |
| ZnSO$_4$.7H$_2$O | 1.5 | 1.5 |
| H$_3$BO$_3$ | 1.6 | 1.6 |
| KI | 0.8 | 0.8 |
| Glycine | 2.0 | 10.0 |
| Thiamine.HCL | 1.0 | 0.5 |
| Pyridoxine.HCL | 0.5 | 0.5 |
| Nicotinic acid | 0.5 | 2.5 |

1.5 mg/l 2,4-D (2,4-dichlorophenoxy acetic acid), 3.0 mg/l NAA (naphthalene acetic acid), 2.5 mg/l kinetin, 3% sucrose, and 1% agar, pH 5.8].

The calli formed 81 to 84 days after the anther incubation were transferred to a regeneration N6 medium [N6 basal medium (see Table 1), 5.0 mg/l BA benzyl adenine), 0.1 mg/l NAA (naphthalene acetic acid), 3% sucrose, and (1% agar, pH 5.8), and the regenerated plants (A1 generation) were grown in a greenhouse to obtain selfed seeds (A2).

The A2 lines were grown in the Kasai Experimental Farm, and were investigated for glabrous variations. The sowing and transplantation were made on Jun. 6, and Jun. 28, 1988, respectively. Single 24 plants were examined per line. The results will be shown later.

EXAMPLE 2

A japonica-type rice variety "Koganebare" was used as a plant material for an anther culture of the present invention. The seeds were sown in May 1986, and the seedlings were transplanted in Jun. to the experimental field in Kasai. Immature spikelets containing the microspores at the middle to late uninucleate stage were sampled on Aug. 21, 1986, and these immature spikelets with leaf sheaths were covered with gauze moistened with water, further covered with aluminum foil, placed in a plastic bag, and treated of 5° C. for 7 days.

The pretreated immature spikelets were immersed in an 80% aqueous solution of ethanol for ca. 1 min and washed 2 to 3 times with sterilized water on a clean bench. Immature anthers were excised with a pair of tweezers, and incubated on a callus-inducing N6 medium [N6 basal medium (see Table 1), 2 mg/l 2,4-D (2,4-dichlorophenoxy acetic acid), 0.5 mg/l BA (benzyl adenine), 3% sucrose, and 1% agar, pH 5.8]. The calli formed 82 to 83 days after the anther incubation were transferred to a regeneration N6 medium [N6 basal medium (see Table 1), 5.0 mg/l BA (benzyl adenine), 0.1 mg/l NAA (naphthalene acetic acid), 3% sucrose, and 1% agar, pH 5.8]. The regenerated plants (A1 generation) were groun in a greenhouse to obtain selfed seeds (A2).

The A2 lines were grown in the Kasai Experimental Farm, and were investigated for glabrous variations. The sowing and transplantation were carried out on Jun. 6 and Jun. 28, 1988, respectively. Single 24 plants were examined per line. The results will be shown later.

EXAMPLE 3

The F$_1$ hybrid from the cross of variety "Akihikari" with variety "Hoshinohikari" was used as a plant material for an anther culture of the present invention. The seeds were sown in May 1988, and the seedlings were transplanted in Jun. to the experimental field in Kasai Immature spikelets containing the microspores at the middle to late uninucleate stage were sampled on Aug. 18, 1988. The immature spikelets with leaf sheaths were covered with gauze moistened with water, further covered with aluminum foil, placed in a plastic bag, and treated at a temperature of 5° C. for 7 days.

The pretreated immature spikelets were immersed in an 80% aqueous solution of ethanol for ca. 1 min, and washed 2 to 3 times with sterilized water on a clean bench. Immature anthers were excised with a pair of tweezers, and incubated on a callus-inducing SK medium [SK basal medium (see Table 1), 2 mg/l 2,4-D (2,4-dichlorophenoxy acetic acid) 0.5 mg/l BA (benzyl adenine), 3% sucrose, and 0.9% agar, pH 5.80]. The calli formed 100 to 102 days after the anther incubation were transferred to regeneration SK medium [SK basal medium (see Table 1), 2.5 mg/l BA (benzyl adenine), 0.1 mg/l NAA (naphtalene acetic acid), 5% sucrose, and 0.9% agar, pH 5.8], and the plants (A1 generation) were grown in a greenhouse to obtain selfed seeds (A2).

The A2 lines were grown in the Kasai Experimental Farm, and were investigated for glabrous variation. The sowing and transplantation were carried out on May 31, and Jun. 21, 1989, respectively. Single 24 plants were examined per line. The results will be shown later.

RESULTS OF EXAMPLES (A) High frequency of occurrence of glabrousness

TABLE 2

Comparison of anther culture breeding of present invention with conventional mutation breeding with respect to mutagenicity thereof in practical characters

| | Breeding Method | | | | | | |
|---|---|---|---|---|---|---|---|
| | Anther culture breeding[1] | | Mutation breeding | | | | |
| | | | Induced variation | | | | |
| | Glabrousness | Glabrousness | Glabrousness | Chlorosis | 5-BU[2] Chlorosis | 2-AP[3] maturing | X-ray[4] maturing | Neutron γ-ray[6] maturing |
| | | | Variety used | | | | | |
| | Nipponbare | Koganebare | (Akihikari × Hoshinohikari) F1 | Ginbozu | Ginbozu | Norin 8 | Norin 8 | Norin 8 |
| Frequency of occurrence of variants (%) | 3.9 | 25.0 | 11.1 | 1.0 | 0.57 | 1.0 | 2.6 | 1.7 |

Note:
[1] Present results.
[2] 5-bromouracil, T. Kawai, and H. Sato (1969), Bull. Nalt. Int. Agri. Sci. D20:1.
[3] 2-aminopurine, T. Kawai, and H. Sato (1969), Bull. Nalt. Int. Agri. Sci. D20:1.
[4] M. Inoue, S. Mori, S. Hori, and H. Yamakake (1971). Japan. J. Breed. 21, Suppl. Vol. 2, P. 168.
[5] M. Inoue, S. Mori, S. Hori, and H. Yamakake (1971). Japan. J. Breed. 21, Suppl. Vol. 2, P. 168.
[6] M. Inoue, S. Mori, S. Hori, and H. Yamakake (1971). Japan. J. Breed. 21, Suppl. Vol. 2, P. 168.

TABLE 3

Comparison of glabrous variation with other variation such as maturity in anther culture breeding

| (1) Induced variation | Variety used | | | Average |
|---|---|---|---|---|
| | Nipponbare | Koganebare | (Akihikari × Hoshinohikari) F1 | |
| Glabrousness | 3.9 | 25.0 | 11.1 | 13.3 |
| Maturity | 3.9 | 6.3 | — | 3.4 |

Note:
The present inventors confirmed the high frequency of occurrence of glabrousness by anther culture for the first time. Since there has been no record found depending on other mutation operations, the other forms of variations were found from the references listed and given as forms of variation.

(B) Results of the present invention (another culture) in short Period in comparison with cross-breeding.

TABLE 4

History of Breeding of Glabrous Varieties by Process of Present Invention and Conventional Crossbreeding

| Year | Anther culture breeding for "new glabrous variety" | Cross breeding for Akenohoshi |
|---|---|---|
| 1971 | | Intervarietal cross |
| 1971 | | Selection of individuals |
| 1971 | | Trial for individual |
| 1980 | | |
| 1981 | | |
| 1982 | | Test of best families |
| 1983 | | |
| 1984 | | Establishment as variety |
| 1985 | | |
| 1986 | Anther culture & selfing | |
| 1987 | Selection and trial for individual lines | |
| 1988 | Test of best families and establishment as variety | |
| Period required for breeding | 3 years | 13 years |

(C) Evidence that new variety of present invention does not differ from original variety in characteristics other than glabrousness (1) Example of comparison in morphology

TABLE 5

Comparison of "New Glabrous Variety" (SUMIRICE II) Bred by Present Invention and Original Variety

| Characteristics | "New glabrous variety" (present Invention) | Koganebare (Original variety) |
|---|---|---|
| Heading date | Aug. 27 | Aug. 28 |
| Culm length | 76.5 cm | 77.2 cm |
| Spikelet length | 19.0 | 19.1 |
| No. of spikelets (No./plant) | 10.1 | 10.3 |
| Total dry matter weight (kg/a) | 134.8 | 127.6 |
| Weight of hulled rice (kg/a) | 46.8 | 44.5 |
| Quality of brown rice (Score*) | 3.8 | 3.8 |
| Pubescence | none | present |

*1 Score 1 (high)–9 (low)

(2) Comparison of Physiology

As shown in Table 6, the resistance to rice blast disease of the "New Variety" and other control variations were examined. No symptoms occurred under the conditions of an occurrence of the disease with rice having +, Pi-a and Pi-k genes, showing the variety had the same Pi-i and Pi-a genes as Koganebare.

TABLE 6

| Line name | Test No. of Field Resistance to Rice Blast Disease | |
|---|---|---|
| | Genotype | Degree of disease |
| "New Glabrous Variety" (SUMIRICE II) | Pi-i, Pi-a* | 0.0 |
| Parental variety Koganebare | Pi-i, Pi-a | 0.0 |
| Shin 2 | + | 3.6 |
| Sasanishiki | Pi-a | 3.3 |
| Ishikarishiroge | Pi-i | 0.0 |
| Kanto. 51 | Pi-k | 1.0 |

Note:
The variety did not become diseased under the conditions in which the rice blast disease true resistance gene +, Pi-a and Pi-k was not effective. An investigation was made of the rice blast disease true resistance genes, and as a result, it was found the variety had the same Pi-i and Pi-a as Koganebare.
*The genotype for rice blast disease of the variety of the present invention was confirmed by the method of examination of a true resistance to rice blast disease (four repetitions, average for four).

(D) Characteristics of variety of present invention (SUMIRICE II).

(1) Variety bred by anther culture using Koganebare as original variety.

Plant type: Partial panicle weight type
The culm length is the same or slightly shorter than Nipponbare.
The culm thickness is slightly greater.
The leaves are glabrous.
The flag leaf stand straighter than Nipponbare.
The plant habit is good.
The resistance to lodging is strong.
The hull color is a yellowish white.
The endsperm is nonglutinous.
The yield is greater than Nipponbare and the same or better than Koganebare.
The heading date is the same as Koganebare.
No shattering habit exists.
Disease resistance: Regarding the resistance to rice blast disease, no disease occurred under conditions where varieties having +, Pi-a, and Pi-k genes become diseased, and by examination of the true resistance to rice blast disease, it was confirmed that the variety has the same Pi-i and Pi-a as Koganebare.
The resistance to rice stripe disease is poor, as for Koganebare.
The heading date is 3 to 4 days earlier than the conventional glabrous variety Akenohoshi.
A clear differentiation from other varieties is possible due to the above characteristics.

(2) Example of evaluation test of line showing that variety formed by anther culture using Koganebare as original variety is genetically fixed.

Five lines were made in the next generation based on five plants selected at random from the preceding generation. To investigate the genetic fixation for the five lines, an analysis of the variance was performed for the culm length, spikelet length, and number of spikelets.

The results are shown in Table 7 and Table 8. No significant difference was observed for any of the forms. This enables the conclusion that the average values of the lines are statistically equal and genetically uniform.

Date sown: May 24

Date transplanted: June 20
Planting density: Single 24 plants per line, 22.2 plants/m$^2$ (30 cm × 15 cm)

Fertilization (kg/10 a)

| | N | P$_2$O$_5$ | K$_2$O |
|---|---|---|---|
| Basal fertilization | 5.0 | 5.0 | 5.0 |
| Ear fertilization I (15 days before heading) | 1.0 | 0.1 | 1.2 |
| Ear fertilization II (5 days before heading) | 2.0 | 0.3 | 2.4 |

Control: Control performed in accordance with usual control system

TABLE 7

Results of Evaluation Test of Lines of Line Groups

| Line | Heading date | Culm length (cm) | Spikelet length (cm) | No. of Spikelets (No./plant) |
|---|---|---|---|---|
| SUMIRICE II | | | | |
| C41 | Aug. 25 | 75.0 | 19.7 | 10.8 |
| C42 | Aug. 25 | 76.2 | 21.0 | 11.2 |
| C43 | Aug. 25 | 78.6 | 20.3 | 11.8 |
| C44 | Aug. 25 | 74.0 | 20.9 | 10.6 |
| C45 | Aug. 25 | 75.8 | 20.2 | 12.0 |
| Average | Aug. 25 | 75.9 | 20.4 | 11.3 |
| Control. | | | | |
| Nipponbare | Aug. 25 | 84.6 | 20.9 | 10.8 |
| Koganebare | Aug. 25 | 78.2 | 20.4 | 12.2 |

Note:
No significant differences were observed among all lines for culm length, spikelet length, and number of spikelets.

TABLE 8

Results of Analysis of Variance for Culm Length, Spikelet Length, and Number of Spikelets

| Source of variation | Degree of freedom | Sum of square | Mean square | F |
|---|---|---|---|---|
| Culm Length | | | | |
| Between lines | 4 | 59,0400 | 14,760 | 3.57 ns |
| Error | 20 | 114,8000 | 5,740 | |
| Total | 24 | 173,8400 | | |
| Spikelet Length | | | | |
| Between lines | 4 | 5,5680 | 1,392 | 0.79 ns |
| Error | 20 | 35,2120 | 1,761 | |
| Total | 24 | 40,7800 | | |
| Number of Spikelets | | | | |
| Between lines | 4 | 7,4400 | 1,860 | 0.31 ns |
| Error | 20 | 119,6000 | 5,980 | |
| Total | 24 | 127,0400 | | | ns: Not significant.

The process of breeding a glabrous variety by tissue culture according to the present invention gives an extreme high occurrence of glabrousness compared with the conventional cross breeding and artificial mutation breeding methods, and features an extremely short raising period (see Table 2 to Table 4). Further, according to the process of the present invention, the new variety having desired and useful characteristics is an extremely effective invention in that even conventional useful pubescent varieties can be easily made into glabrous varieties in a short time and with a high reliability, without changing useful characteristics other than the glabrousness.

Further, the glabrous variety raised, as mentioned earlier, increases the work efficiency during the cultivation of rice plants, in particular during the harvesting and processing (hulling, etc.), and further, does not change the other useful characteristics, and thus has an extremely high use efficiency.

We claim:

1. A process for producing a genetically fixed glabrous, japonica-type rice variety derived from a japonica-type rice variety selected from the group consisting of "Nipponbare", "Koganebare", and a F1 hybrid from the cross of a variety "Akihikari" with a variety "Hoshinohikari" which comprises culturing anther from a plant of a japonica-type rice variety on a callus-inducing medium containing 2.5–7.0 mg/l of a callus-inductively effective amount of plant hormones which are a mixture of auxin, selected from the group consisting of 2,4-D, NAA, and a mixture of 2,4-D and NAA, and cytokinin, selected from the group consisting of kinetin and BA, in which the concentration of auxin is 1.5–2.0 mg/l higher than the concentration of cytokinin to produce calli, culturing said calli on a regeneration medium containing 2.6–5.1 mg/l of a regeneratively effective amount of plant hormones which are a mixture of said cytokinin and said auxin in which the concentration of cytokinin is 2.4–4.9 mg/l higher than the concentration of auxin, growing the regenerants, and selecting glabrous plants, whereby the agronomic characteristics other than glabrousness of the rice variety are essentially unchanged.

2. A method of producing seeds of a genetically fixed glabrous, japonica-type rice variety produced by the process of claim 1, which comprises sexually reproducing a plant of said variety and recovering seeds obtained as a result of said sexual reproduction.

3. A process for producing the genetically fixed glabrous rice variety derived from a japonica-type rice variety "Koganebare" which comprises culturing another from a plant of a japonica-type rice variety "Koganebare" on a callus-inducting medium containing 2.5–7.0 mg/l of callus-inductively effective amount of plant hormones which are a mixture of auxin, selected from the group consisting of 2,4-D, NAA, and a mixture of 2,4-D and NAA, and cytokinin, selected from the group consisting of Kinetin and BA, in which the concentration of auxin, is 1.5–2.0 mg/l higher than the concentration of cytokinin to produce calli, culturing said calli on a regeneration medium containing 2.6–5.1 mg/l of regeneratively effective amount of plant hormones which are a mixture of said cytokinin and said auxin in which the concentration of cytokinin is 2.4–4.9 mg/l higher than the concentration of auxin, growing the regenerants, and selecting glabrous plants, whereby the agronomic characteristics other than glabrousness of the rice variety are essentially unchanged.

4. A method of producing seeds of a genetically fixe glabrous, japonica-type rice variety derived from a japonica-type rice variety "Koganebare" produced by the process of claim 3, which comprises sexually reproducing a plant of said genetically fixed glabrous, japonica-type rice variety and recovering seeds obtained as a result of said sexual reproduction.

* * * * *